US010893870B2

(12) United States Patent
Wang et al.

(10) Patent No.: US 10,893,870 B2
(45) Date of Patent: Jan. 19, 2021

(54) VASO-OCCLUSIVE DEVICE (71) Applicants: STRYKER CORPORATION, Kalamazoo, MI (US); STRYKER EUROPEAN HOLDINGS I, LLC, Kalamazoo, MI (US)

(72) Inventors: Jiaxu Wang, Salt Lake City, UT (US); Andrew S. Lee, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 279 days.

(21) Appl. No.: 15/970,805

(22) Filed: May 3, 2018

(65) Prior Publication Data
US 2019/0336138 A1 Nov. 7, 2019

(51) Int. Cl.
*A61B 17/12* (2006.01)
*A61F 2/01* (2006.01)

(52) U.S. Cl.
CPC .. *A61B 17/12177* (2013.01); *A61B 17/12113* (2013.01); *A61B 17/12145* (2013.01);
(Continued)

(58) Field of Classification Search
CPC .............. A61F 2/90; A61F 2250/0098; A61F 2002/3008; A61F 2/86; A61F 2002/016; A61F 2002/823; A61F 2002/825; A61F 2250/0017; A61F 2250/0039; A61F 2/885; A61F 2/2418; A61F 2/2412;
(Continued)

(56) References Cited

U.S. PATENT DOCUMENTS 4,994,069 A 2/1991 Ritchart et al.
5,876,445 A * 3/1999 Andersen ................ A61F 2/958
623/23.7
(Continued)

FOREIGN PATENT DOCUMENTS

EP 0894503 A2 6/1998
WO WO 2019/158628 * 8/2019

OTHER PUBLICATIONS

PCT International Search Report and Written Opinion for International Appln. No. PCT/USZ019/030136, Applicant Stryker Corporation, dated Aug. 1, 2019 (10 pages).

*Primary Examiner* — Katherine M Shi
(74) *Attorney, Agent, or Firm* — Vista IP Law Group, LLP (57) ABSTRACT

A vaso-occlusive device includes an inner braided member having an unconstrained deployed configuration and a constrained delivery configuration. The inner braided member includes a first plurality of filaments made of a first material composition, where a pair of filaments of the first plurality defines a first braid angle when the inner braided member is in the deployed configuration. The device also includes an outer braided member disposed at least partially around the inner braided member, and having an unconstrained deployed configuration and a constrained delivery configuration. The outer braided member includes a second plurality of filaments made of a second material composition different from the first material, where the first material has a greater radiopacity than the second material. A pair of filaments of the second plurality defines a second braid angle, substantially equal to the first braid angle, when the outer braided member is in the deployed configuration.

20 Claims, 9 Drawing Sheets (52) U.S. Cl.
CPC .............. *A61B 2017/12054* (2013.01); *A61F 2002/016* (2013.01)

(58) Field of Classification Search
CPC ................. A61F 2/2409; A61F 2/2427; A61F 2210/0014; A61F 2/2445; A61B 17/1214; A61B 17/12172; A61B 17/12022; A61B 17/12109; A61B 90/39; A61B 17/12113; A61B 17/12177; A61B 17/12145; A61B 17/12163; A61B 2017/00243; A61B 2017/00783
See application file for complete search history.

(56) References Cited

U.S. PATENT DOCUMENTS

| | | | |
|---|---|---|---|
| 10,321,915 B2 | 6/2019 | Murphy et al. | |
| 2001/0056296 A1* | 12/2001 | Sugita | A61F 2/90 623/1.15 |
| 2006/0206201 A1* | 9/2006 | Garcia | A61B 17/12022 623/1.51 |
| 2007/0112415 A1* | 5/2007 | Bartlett | A61F 2/90 623/1.15 |
| 2009/0062841 A1* | 3/2009 | Amplatz | A61B 17/12022 606/200 |
| 2009/0259125 A1* | 10/2009 | Stinson | A61B 17/12022 600/431 |
| 2009/0312834 A1* | 12/2009 | Wood | A61F 2/90 623/1.44 |
| 2011/0224707 A1* | 9/2011 | Miloslavski | A61B 17/221 606/159 |

* cited by examiner

VASO-OCCLUSIVE DEVICE

FIELD

The field of the disclosed embodiments generally relates to vaso-occlusive devices for establishing an embolus or vascular occlusion in a vessel of a human patient. More particularly, the disclosed embodiments relate to at least partially braided or woven vaso-occlusive devices, and radiopaque features thereof.

BACKGROUND

Vaso-occlusive devices or implants are used for a wide variety of reasons, including treatment of intra-vascular aneurysms. Commonly used vaso-occlusive devices include soft, helically wound coils formed by winding a platinum (or platinum alloy) wire strand about a "primary" mandrel. The coil is then wrapped around a larger, "secondary" mandrel, and heat treated to impart a secondary shape. For example, U.S. Pat. No. 4,994,069, issued to Ritchart et al., which is fully incorporated herein by reference as though set forth in full, describes a vaso-occlusive device that assumes a linear, helical primary shape when stretched for placement through the lumen of a delivery catheter, and a folded, convoluted secondary shape when released from the delivery catheter and deposited in the vasculature. Other examples of vaso-occlusive devices include at least partially braided or woven devices, such as those described in U.S. patent application Ser. No. 15/542,924, by Murphy et al., which is fully incorporated herein by reference as though set forth in full.

In order to deliver the vaso-occlusive devices to a desired site in the vasculature, e.g., within an aneurysmal sac, it is well-known to first position a small profile, delivery catheter or "micro-catheter" at the site using a steerable guidewire. Typically, the distal end of the micro-catheter is provided, either by the attending physician or by the manufacturer, with a selected pre-shaped bend, e.g., 45°, 26°, "J", "S", or other bending shape, depending on the particular anatomy of the patient, so that it will stay in a desired position for releasing one or more vaso-occlusive device(s) into the aneurysm once the guidewire is withdrawn. A delivery or "pusher" assembly or "wire" is then passed through the micro-catheter, until a vaso-occlusive device pushed by a distal end of the delivery assembly is extended out of the distal end opening of the micro-catheter and into the aneurysm. Once in the aneurysm, portions of the vaso-occlusive device deform or bend to allow more efficient and complete packing. Vaso-occlusive devices that are coupled to the distal end of the delivery assembly are released or "detached" from the distal end of the delivery assembly, after extending into the aneurysm. Then, the delivery assembly is withdrawn back through the catheter. Depending on the particular needs of the patient, one or more additional vaso-occlusive devices may be pushed through the catheter and released at the same site.

Some vaso-occlusive devices include radiopaque features to facilitate visualization during delivery. Further, in order to better frame and fill aneurysms, complex three-dimensional secondary shapes can be imparted on vaso-occlusive devices and the stiffness/flexibility of vaso-occlusive devices can be modified. However, vaso-occlusive devices continue to have performance limitations including radiopacity, shape retention, and flexibility.

While some vaso-occlusive devices, such as those incorporating drawn filled tubes, attempt to address limitations of current vaso-occlusive devices, many of these are compromise solutions that balance limitations against each other. Accordingly, there remains a need for vaso-occlusive devices that address these limitations.

SUMMARY

In one embodiment, a vaso-occlusive device includes an inner braided member having an unconstrained deployed configuration and a constrained delivery configuration. The inner braided member includes a first plurality of filaments made of a first material composition, where a pair of filaments of the first plurality defines a first braid angle when the inner braided member is in the deployed configuration. The device also includes an outer braided member disposed at least partially around the inner braided member, and having an unconstrained deployed configuration and a constrained delivery configuration. The outer braided member includes a second plurality of filaments made of a second material composition different from the first material composition, where the first material composition has a greater radiopacity than the second material composition. A pair of filaments of the second plurality defines a second braid angle, substantially equal to the first braid angle, when the outer braided member is in the deployed configuration.

In one or more embodiments, the filaments of the first plurality have circular cross-sections with diameters ranging from about 0.0005" to about 0.003". The filaments of the first plurality may have non-circular cross-sections. The filaments of the first plurality may have rectangular cross-sections. The first plurality of filaments may consist of 2 to 12 filaments. The first material composition may include one or more materials selected from the group consisting of a Pt group metal, Ta, Au, and alloys thereof.

In one or more embodiments, the filaments of the second plurality have circular cross-sections with diameters ranging from about 0.0005" to about 0.003". The filaments of the second plurality may have non-circular cross-sections. The filaments of the first plurality may have rectangular cross-sections. The second plurality of filaments may consist of 16-96 filaments. The second plurality of filaments may consist of 24 filaments. The second material composition may include a superelastic alloy. The second material composition may include NiTi.

In one or more embodiments, the inner braided member and the outer braided member are attached to each other at one or more attachment locations. The inner braided member and the outer braided member may be attached to each other at respective first ends thereof. The inner braided member and the outer braided member may be attached to each other at respective first and second ends thereof. The braided occlusive device may have a flattened cross-section.

In one or more embodiments, the pair of filaments of the first plurality defines a third braid angle when the inner braided member is in the delivery configuration. The pair of filaments of the second plurality defines a fourth braid angle, substantially equal to the third braid angle, when the outer braided member is in the delivery configuration. The second material may have a greater superelasticity than the first material.

In another embodiment, a vaso-occlusive device includes an inner bent member having an unconstrained deployed configuration and a constrained delivery configuration. The inner bent member includes a first plurality of sections made of a first material composition, where a pair of sections of the first plurality defines a first angle when the inner bent member is in the deployed configuration. The device also includes an outer braided member disposed at least partially around the inner bent member, the outer braided member having an unconstrained deployed configuration and a constrained delivery configuration. The outer braided member includes a second plurality of filaments made of a second material composition different from the first material composition, where the first material composition has a greater radiopacity than the second material composition. A pair of filaments of the second plurality defines a second braid angle, substantially equal to the first angle, when the outer braided member is in the deployed configuration.

In one or more embodiments, the pair of sections of the first plurality defines a third angle when the inner bent member is in the delivery configuration. The pair of filaments of the second plurality defines a fourth braid angle, substantially equal to the third angle, when the outer braided member is in the delivery configuration. The second material may have a greater superelasticity than the first material.

Other and further aspects and features of the disclosed embodiments will become apparent from the ensuing detailed description in view of the accompanying figures.

BRIEF DESCRIPTION OF THE DRAWINGS

The drawings illustrate the design and utility of various disclosed embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments for purposes of illustration and facilitating the below detailed description, and are not therefore to be considered limiting of its scope.

FIGS. 1A-1D are schematic views of an exemplary vaso-occlusive device constructed according to one embodiment.

FIGS. 2A-2D are schematic views of an exemplary vaso-occlusive device constructed according to one embodiment.

FIGS. 4A-4D are schematic views of an exemplary vaso-occlusive device constructed according to one embodiment.

FIGS. 6A-6D are schematic views of an exemplary vaso-occlusive device constructed according to one embodiment.

DETAILED DESCRIPTION OF THE ILLUSTRATED EMBODIMENTS

This specification describes exemplary embodiments and applications thereof. The disclosure, however, is not limited to these exemplary embodiments and applications or to the manner in which the exemplary embodiments and applications operate or are described herein. Further, the figures may show simplified or partial views, and the dimensions of elements in the figures may be exaggerated or otherwise not in proportion. Moreover, elements of similar structures or functions are represented by like reference numerals throughout the figures. In addition, an illustrated embodiment needs not have all the aspects or advantages shown. An aspect or an advantage described in conjunction with a particular embodiment is not necessarily limited to that embodiment, and can be practiced in any other embodiments even if not so illustrated.

For the following defined terms, these definitions shall be applied, unless a different definition is given in the claims or elsewhere in this specification.

As the terms "on," "attached to," "connected to," "coupled to," "secured to" or similar words are used herein, one element (e.g., a material, a layer, a substrate, etc.) can be "on," "attached to," "connected to," "coupled to" or "secured to" another element regardless of whether the one element is directly on, attached to, connected to, coupled to or secured to the other element or there are one or more intervening elements between the one element and the other element. Directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. The term "ones" means more than one.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure. The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used herein, a plurality of "elongate members" used to form a braid can include only a single elongate member used to form the braid, i.e., wherein the single elongate member turns back on itself at the ends of the braid. As used herein, the terms "tube," "tubular," "diameter," "radius" and "circumference" encompass objects with non-circular cross section as well as those with circular cross sections. As used herein, the terms "stiffness" or "flexibility" as they pertain to braids or portions thereof include, but are not limited to, bending stiffness. As used herein, the term "constrained" includes, but is not limited to, being held in a compressed, elongated configuration due to forces exerted thereon, such as by a delivery catheter. As used herein, the term "unconstrained" includes, but is not limited to, the lack of external forces acting thereon. While "unconstrained" is used synonymously with "deployed" herein, the anatomy of some patients may exert forces on deployed vaso-occlusive devices.

Figure 1A:
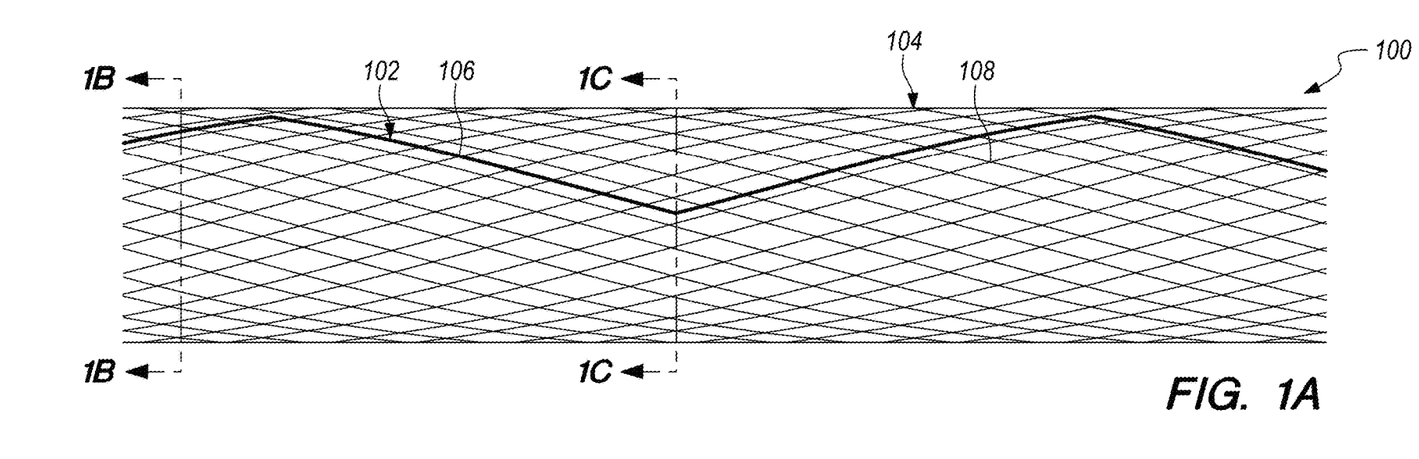
FIG. 1A is a longitudinal schematic view.

FIG. 1A depicts a vaso-occlusive device 100 in an unconstrained deployed configuration with a linear (i.e., unshaped) secondary structure according to one embodiment. The vaso-occlusive device 100 includes an inner bent member 102 and an outer braided member 104. The inner bent member 102 is a radiopaque ("RO") wire 106 with a plurality of sections/filaments 106a, 106b. The RO wire 106 may include any radiopaque substance including, but not limited to, a platinum (Pt) group metal, tantalum (Ta), gold (Au), or various alloys thereof. Exemplary Pt alloys include, but are not limited to, platinum-tungsten (Pt—W) and platinum-iridium (Pt—Ir). The materials included in the RO wire 106 provide radiopacity to the vaso-occlusive device 100. The RO wire 106 may have a circular cross section with a diameter ranging from about 0.0005 inches to about 0.003 inches. In other embodiments, the RO wire 106 may have a noncircular cross-section, such as a rectangular cross-section.

The RO wire 106 forming the inner bent member 102 of the vaso-occlusive device 100 depicted in FIG. 1A includes a plurality of sections/filaments 106a, 106b. Each of the sections/filaments 106a, 106b is approximately linear and has a direction. As shown in FIG. 1D, where the sections/filaments 106a, 106b of the RO wire 106 intersect, they form an angle 110.

The outer braided member 104 includes one or more braid wires 108 with a plurality of sections/filaments 108a, 108b. While the sections/filaments 108a, 108b of the plurality of braid wires 108 may be separate braid wires 108, the sections/filaments 108a, 108b may also be sections or filaments of a single braid wire 108 that is looped back on itself at one or more ends of the outer braided member 104 to provide a plurality of sections/filaments 108a, 108b of the same braid wire 108 that can be woven with each other to form the outer braided member 104. In other embodiments, the outer braided member 104 is woven from a plurality of braid wires 108. In some embodiments, the plurality of braid wires 108 includes 16-96 braid wires 108. In some of those embodiments, the plurality of braid wires 108 includes 24 braid wires 108.

Figure 1B:
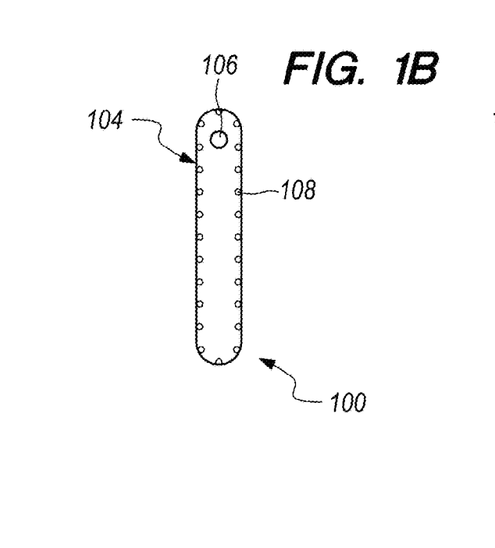
FIGS. 1B and 1C are cross-sectional schematic views.
Figure 1C:
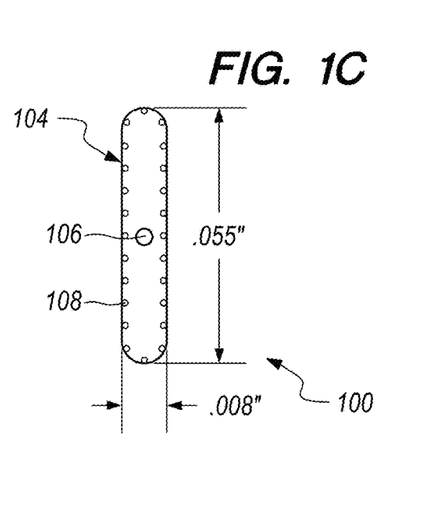
Figure 1D:
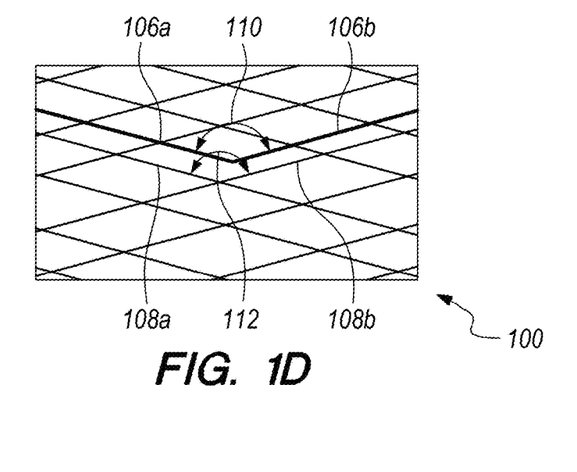
FIG. 1D is a detailed longitudinal schematic view.

As shown in FIGS. 1B and 1C, the outer braided member 104 may have a flat cross-section. FIGS. 1A-1D, the cross-section of the outer braided member 104 has a length of approximately 0.055" and a width of approximately 0.008".

The one or more braid wires 108 may include a super elastic alloy, such as nitinol ("NiTi"). The NiTi composition of the one or more braid wires 108 provides the shape retention and flexibility characteristics desired in a vaso-occlusive device 100. Each of the sections/filaments 108a, 108b is approximately linear and has a direction. As shown in FIG. 1D, where the sections/filaments 108a, 108b of the braid wire 108 intersect, they form an angle 112.

The inner bent member 102 and the outer braided member 104 are configured such that a first angle 110 formed where the sections/filaments 106a, 106b of the RO wire 106 intersect is substantially equal to a second angle 112 formed where the sections/filaments 108a, 108b of the braid wire 108 intersect. As shown in FIG. 1D, the inner bent member 102 and the outer braided member 104 are also configured such that sections/filaments 106a, 106b of the RO wire 106 are substantially parallel to respective sections/filaments 108a, 108b of the braid wire 108. As used herein, the terms "substantial" or "substantially" as applied to quantitative characteristics mean within 10%.

The substantial equivalence between the first and second angles 110, 112 minimizes relative foreshortening of the inner bent member 102 compared to the outer braided member 104 when the vaso-occlusive device 100 transitions from the constrained delivery configuration to an unconstrained deployed configuration. When the vaso-occlusive device 100 is in the constrained delivery configuration, sections/filaments 106a, 106b of the RO wire 106 form a third angle (not shown) and the sections/filaments 108a, 108b of the braid wire 108 form a fourth angle (not shown), that is substantially equal to the third angle. Minimizing relative foreshortening during the transition between the delivery and deployed configurations minimizes changes in characteristics along the length of the vaso-occlusive device 100 during the transition.

The inner bent member 102 and the outer braided member 104 are attached to each other in at least one location along the vaso-occlusive device 100. In some embodiments, the inner bent member 102 and the outer braided member 104 are attached to each other at respective first ends thereof. In some of those embodiments, the inner bent member 102 and the outer braided member 104 are attached to each other at respective first and second ends thereof. With increasing number of attachment locations between the inner bent member 102 and the outer braided member 104, relative foreshortening increases structural strain between the inner bent member 102 and the outer braided member 104. Therefore, minimizing relative foreshortening during the transition between the delivery and deployed configuration also addresses this issue that becomes more important with an increasing number of attachment locations between the inner bent member 102 and the outer braided member 104.

FIGS. 2A-2D depict a vaso-occlusive device 200 in an unconstrained deployed configuration with a linear (i.e., unshaped) secondary structure according to another embodiment. The vaso-occlusive device 200 depicted in FIGS. 2A-2D is similar to the vaso-occlusive device 100 depicted in FIGS. 1A-1D, and similar parts in the two vaso-occlusive devices 100, 200 have similar reference numbers.

The difference between the two vaso-occlusive devices 100, 200 is that instead of an inner bent member 102, the vaso-occlusive device 200 in FIGS. 2A-2D has an inner braided member 202, which includes one or more RO wires 206 with a pair of sections/filaments 206a, 206b. While the sections/filaments 206a, 206b of the plurality of RO wires 206 may be separate RO wires 206, the sections/filaments 206a, 206b may also be sections or filaments of a single RO wire 206 that is looped back on itself at one or more ends of the inner braided member 202 to provide a plurality of sections/filaments 206a, 206b of the same RO wire 206 that can be woven with each other to form the inner braided member 202. In other embodiments, the outer braided member 204 is woven from a plurality of RO wires 206. The RO wires 206 are similar to the RO wires 106 depicted in FIGS. 1A-1D and described above.

Figure 2A:
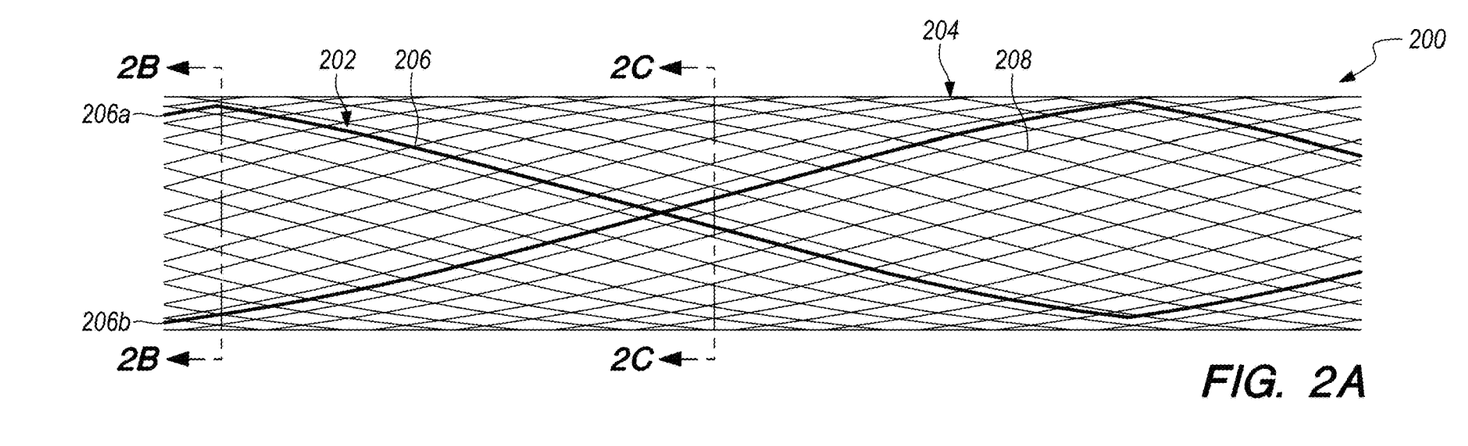
FIG. 2A is a longitudinal schematic view.
Figure 2B:
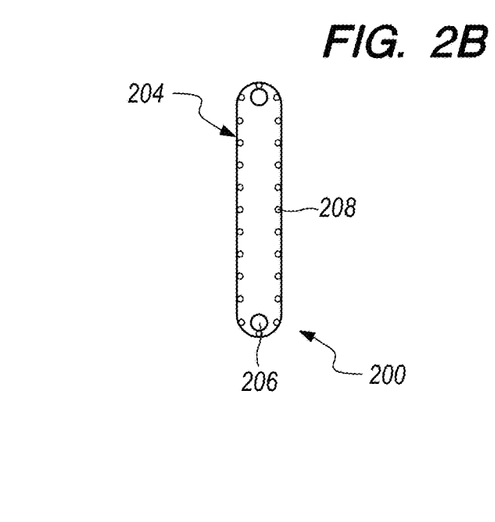
FIGS. 2B and 2C are cross-sectional schematic views.
Figure 2C:
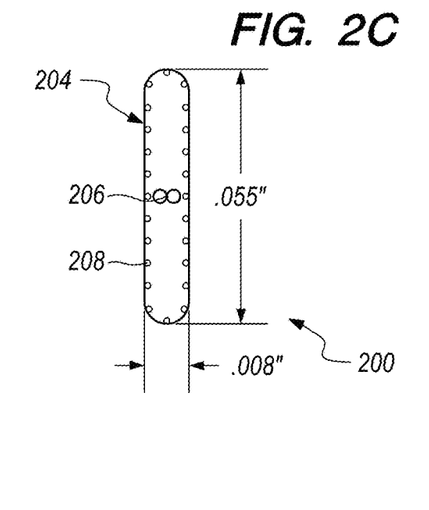

The outer braided member 204 is almost identical to the outer braided member 104 depicted in FIGS. 1A-1D and described above. As described above for the vaso-occlusive device 100 depicted in FIGS. 1A-1D, the braid wires 208 of the outer braided member 204 provide shape retention and flexibility characteristics of the vaso-occlusive device 200. Similarly, the RO wires 206 of the inner braided member 202 provide radiopacity characteristics of the vaso-occlusive device 200. Because the vaso-occlusive device 200 includes more sections/filaments 206a, 206b forming the inner braided member 202 compared to the sections/filaments 106a, 106b forming the inner bent member 102, the outer braided member 204 may have fewer and/or more flexible sections/filaments 208a, 208b to achieve a desired flexibility of the vaso-occlusive device 200. The plurality of sections/filaments 206a, 206b extend longitudinally along the vaso-occlusive device 200 in a zig-zag pattern defining a plurality of bends as shown in Fig. 2A.

Figure 2D:
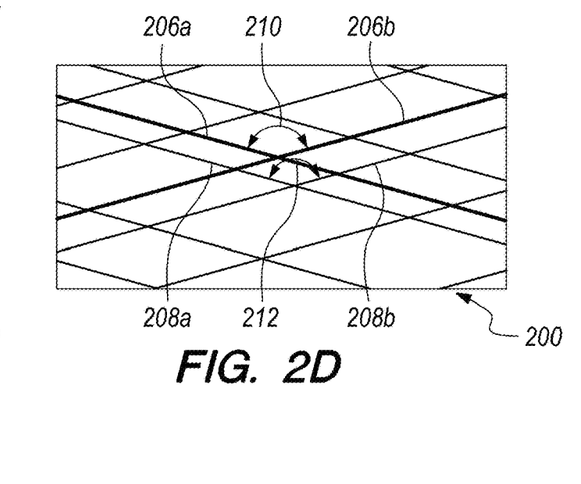
FIG. 2D is a detailed longitudinal schematic view.

The inner braided member 202 and the outer braided member 204 are configured such that a first angle 210 formed where the sections/filaments 206a, 206b of the RO wire 206 intersect is substantially equal to a second angle 212 formed where the sections/filaments 208a, 208b of the braid wire 208 intersect. As shown in FIG. 2D, the inner bent member 202 and the outer braided member 204 are also configured such that sections/filaments 206a, 206b of the RO wire 206 are substantially parallel to respective sections/filaments 208a, 208b of the braid wire 208. When the vaso-occlusive device 200 is in the constrained delivery configuration, sections/filaments 206a, 206b of the RO wire 206 form a third angle (not shown) and the sections/filaments 208a, 208b of the braid wire 208 form a fourth angle (not shown), that is substantially equal to the third angle.

As with the vaso-occlusive device 100 depicted in FIGS. 1A-1D, the substantial equivalence between the first and second angles 210, 212 in vaso-occlusive device 200 minimizes relative foreshortening of the inner braided member 202 compared to the outer braided member 204 when the vaso-occlusive device 200 transitions from the constrained delivery configuration to an unconstrained deployed configuration. Minimizing relative foreshortening during the transition between the delivery and deployed configurations minimizes changes in characteristics along the length of the vaso-occlusive device 200 and structural strain during the transition.

Figure 3:
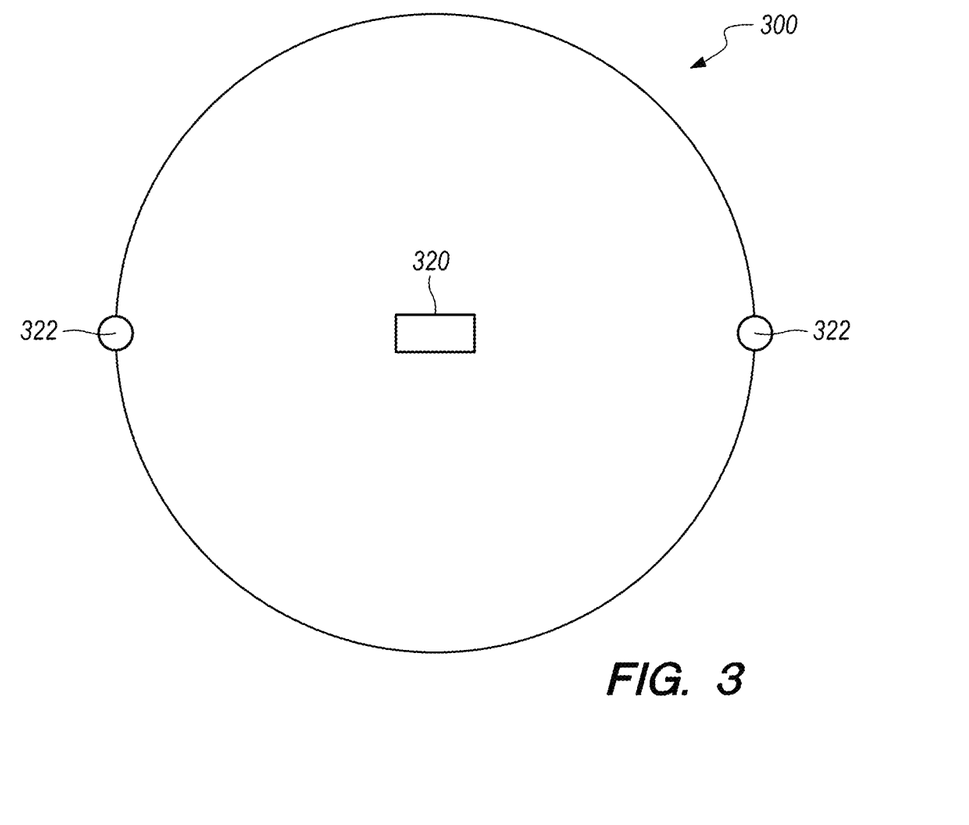
FIG. 3 is a schematic view of a braiding system configured to form the vaso-occlusive device depicted in FIG. 2A according to one embodiment.

FIG. 3 schematically depicts a braiding system 300 configured to form the vaso-occlusive device 200 depicted in FIGS. 2A-2D according to one embodiment. The braiding system 300 includes a mandrel 320 having a flat cross section and a pair of bobbins 322.

In a first step of a method of forming the vaso-occlusive device 200 depicted in FIGS. 2A-2D according to one embodiment, the bobbins 322 are used to braid the one or more RO wires 206 to form the inner braided member 202 on top of the flat mandrel 320. In a second step, the one or more RO wires 206 are heat treated to set the shape of the inner braided member 202. In a third step, the bobbins 322 are used to braid the one or more braid wires 208 to form the outer braided member 204 on top of the inner braided member 202 and the flat mandrel 320. In a fourth step, the one or more braid wires 208 are heat treated to set the shape of the outer braided member 204. In a fifth step, the flat mandrel 320 is removed from the formed vaso-occlusive device 200.

FIGS. 4A-4D depict a vaso-occlusive device 400 in an unconstrained deployed configuration with a linear (i.e., unshaped) secondary structure according to still another embodiment. The vaso-occlusive device 400 depicted in FIGS. 4A-4D is similar to the vaso-occlusive device 200 depicted in FIGS. 2A-2D, and similar parts in the two vaso-occlusive devices 200, 400 have similar reference numbers.

The difference between the two vaso-occlusive devices 200, 400 is that the inner braided member 402 in the vaso-occlusive device 400 in FIGS. 4A-4D includes one or more RO wires 406 with three sections/filaments 406a, 406b, 406c. While the sections/filaments 406a, 406b, 406c of the plurality of RO wires 406 may be separate RO wires 406, the sections/filaments 406a, 406b, 406c may also be sections or filaments of a single RO wire 406 that is looped back on itself at one or more ends of the inner braided member 402 to provide a plurality of sections/filaments 406a, 406b, 406c of the same RO wire 406 that can be woven with each other to form the inner braided member 402. In other embodiments, the outer braided member 404 is woven from a plurality of RO wires 406. The RO wires 406 are similar to the RO wires 206 depicted in FIGS. 2A-2D and described above.

The outer braided member 404 is almost identical to the outer braided member 204 depicted in FIGS. 2A-2D and described above. As described above for the vaso-occlusive device 200 depicted in FIGS. 2A-2D, the braid wires 408 of the outer braided member 404 provide shape retention and flexibility characteristics of the vaso-occlusive device 400. Similarly, the RO wires 406 of the inner braided member 402 provide radiopacity characteristics of the vaso-occlusive device 400. Because the vaso-occlusive device 400 includes more sections/filaments 406a, 406b, 406c forming the inner braided member 402 compared to the sections/filaments 206a, 206b forming the inner bent member 202, the outer braided member 404 may have fewer and/or more flexible sections/filaments 408a, 408b to achieve a desired flexibility of the vaso-occlusive device 400.

Figure 4A:
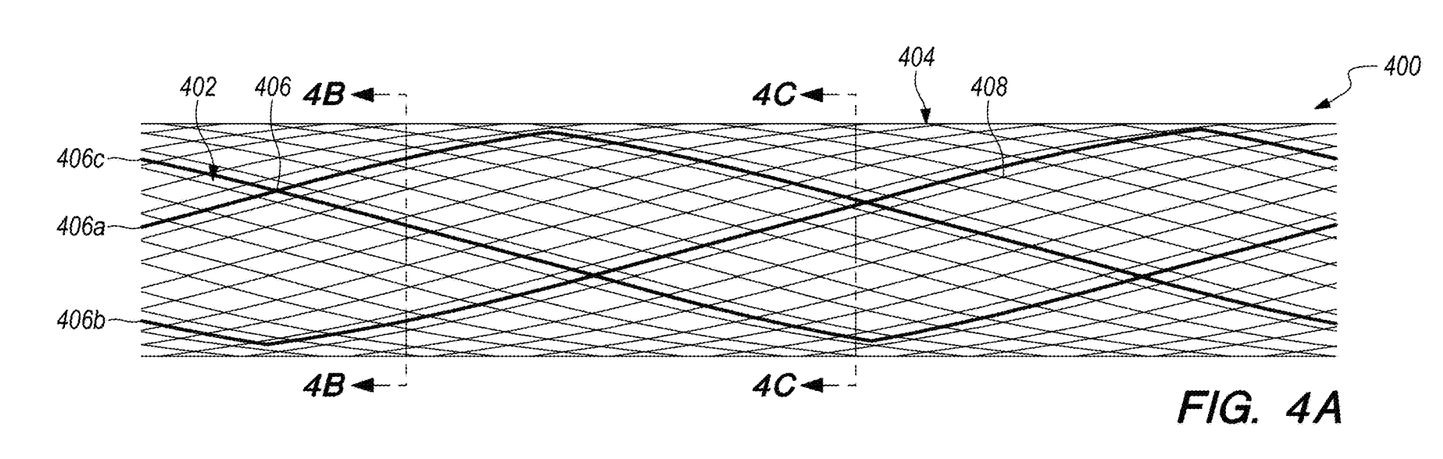
FIG. 4A is a longitudinal schematic view.
Figure 4B:
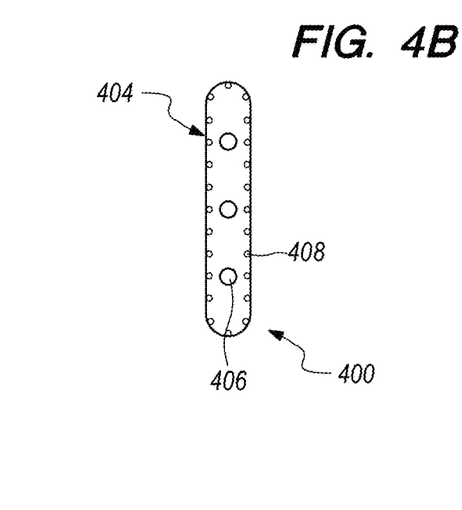
FIGS. 4B and 4C are cross-sectional schematic views.
Figure 4C:
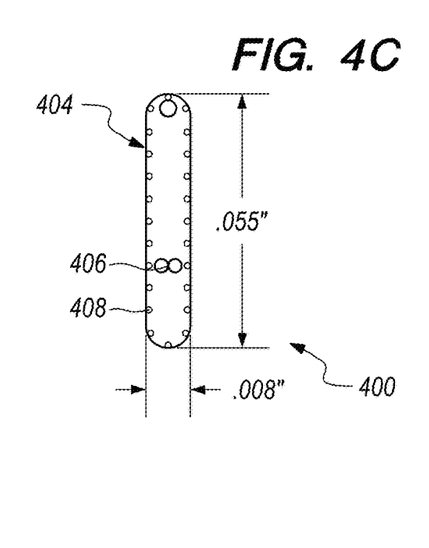
Figure 4D:
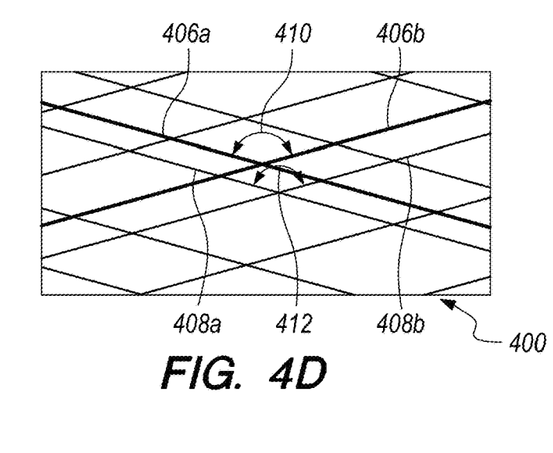
FIG. 4D is a detailed longitudinal schematic view.

The inner braided member 402 and the outer braided member 404 are configured such that a first angle 410 formed where the sections/filaments 406a, 406b, 406c of the RO wire 406 intersect is substantially equal to a second angle 412 formed where the sections/filaments 408a, 408b of the braid wire 408 intersect. As shown in FIG. 4D, the inner bent member 402 and the outer braided member 404 are also configured such that sections/filaments 406a, 406b, 406c of the RO wire 406 are substantially parallel to respective sections/filaments 408a, 408b of the braid wire 408. When the vaso-occlusive device 400 is in the constrained delivery configuration, sections/filaments 406a, 406b, 406c of the RO wire 406 form a third angle (not shown) and the sections/filaments 408a, 408b of the braid wire 408 form a fourth angle (not shown), that is substantially equal to the third angle.

As with the vaso-occlusive device 100 depicted in FIGS. 1A-1D, the substantial equivalence between the first and second angles 410, 412 in vaso-occlusive device 400 minimizes relative foreshortening of the inner braided member 402 compared to the outer braided member 404 when the vaso-occlusive device 400 transitions from the constrained delivery configuration to an unconstrained deployed configuration. Minimizing relative foreshortening during the transition between the delivery and deployed configurations minimizes changes in characteristics along the length of the vaso-occlusive device 400 and structural strain during the transition.

Figure 5:
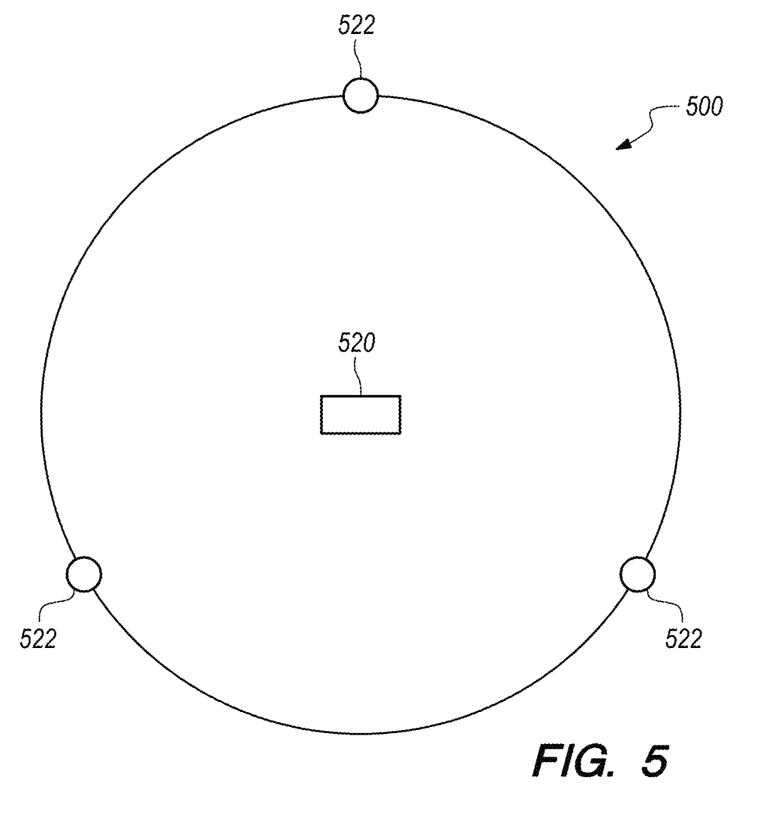
FIG. 5 is a schematic view of a braiding system configured to form the vaso-occlusive device depicted in FIG. 4A according to one embodiment.

FIG. 5 schematically depicts a braiding system 500 configured to form the vaso-occlusive device 400 depicted in FIGS. 4A-4D according to one embodiment. The braiding system 500 includes a mandrel 520 having a flat cross section and three bobbins 522.

In a first step of a method of forming the vaso-occlusive device 400 depicted in FIGS. 4A-4D according to one embodiment, the bobbins 522 are used to braid the one or more RO wires 406 to form the inner braided member 402 on top of the flat mandrel 520. In a second step, the one or more RO wires 406 are heat treated to set the shape of the inner braided member 402. In a third step, the bobbins 522 are used to braid the one or more braid wires 408 to form the outer braided member 404 on top of the inner braided member 402 and the flat mandrel 520. In a fourth step, the one or more braid wires 408 are heat treated to set the shape of the outer braided member 404. In a fifth step, the flat mandrel 520 is removed from the formed vaso-occlusive device 400.

FIGS. 6A-6D depict a vaso-occlusive device 600 in an unconstrained deployed configuration with a linear (i.e., unshaped) secondary structure according to yet another embodiment. The vaso-occlusive device 600 depicted in FIGS. 6A-6D is similar to the vaso-occlusive device 200 depicted in FIGS. 2A-2D, and similar parts in the two vaso-occlusive devices 200, 600 have similar reference numbers.

The difference between the two vaso-occlusive devices 200, 600 is that the inner braided member 602 in the vaso-occlusive device 600 in FIGS. 6A-6D includes one or more RO wires 606 with four sections/filaments 606a, 606b, 606c, 606d. While the sections/filaments 606a, 606b, 606c, 606d of the plurality of RO wires 606 may be separate RO wires 606, the sections/filaments 606a, 606b, 606c, 606d may also be sections or filaments of a single RO wire 606 that is looped back on itself at one or more ends of the inner braided member 602 to provide a plurality of sections/filaments 606a, 606b, 606c, 606d of the same RO wire 606 that can be woven with each other to form the inner braided member 602. In other embodiments, the outer braided member 604 is woven from a plurality of RO wires 606. The RO wires 606 are similar to the RO wires 206 depicted in FIGS. 2A-2D and described above.

The outer braided member 604 is almost identical to the outer braided member 204 depicted in FIGS. 2A-2D and described above. As described above for the vaso-occlusive device 200 depicted in FIGS. 2A-2D, the braid wires 608 of the outer braided member 604 provide shape retention and flexibility characteristics of the vaso-occlusive device 600. Similarly, the RO wires 606 of the inner braided member 602 provide radiopacity characteristics of the vaso-occlusive device 600. Because the vaso-occlusive device 600 includes more sections/filaments 606a, 606b, 606c, 606d forming the inner braided member 602 compared to the sections/filaments 206a, 206b forming the inner bent member 202, the outer braided member 604 may have fewer and/or more flexible sections/filaments 608a, 608b to achieve a desired flexibility of the vaso-occlusive device 600.

Figure 6A:
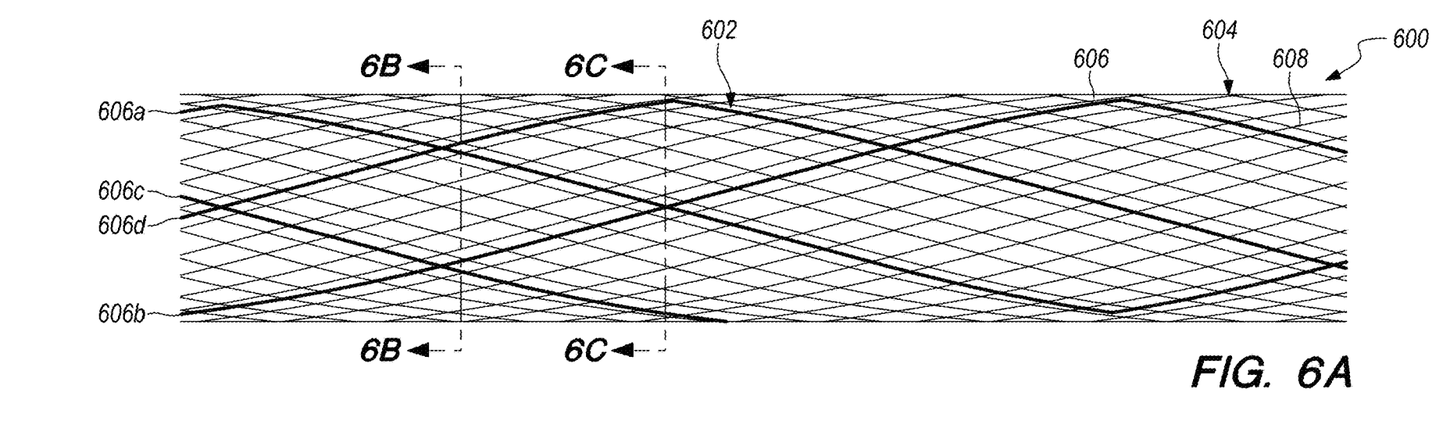
FIG. 6A is a longitudinal schematic view.
Figure 6B:
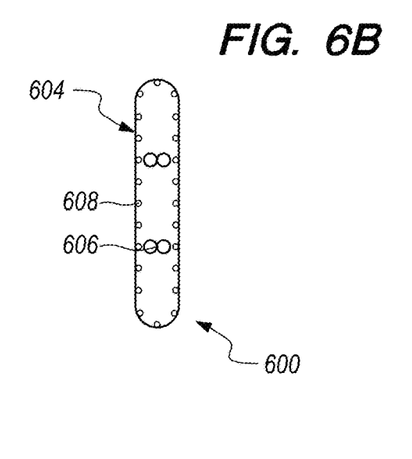
FIGS. 6B and 6C are cross-sectional schematic views.
Figure 6C:
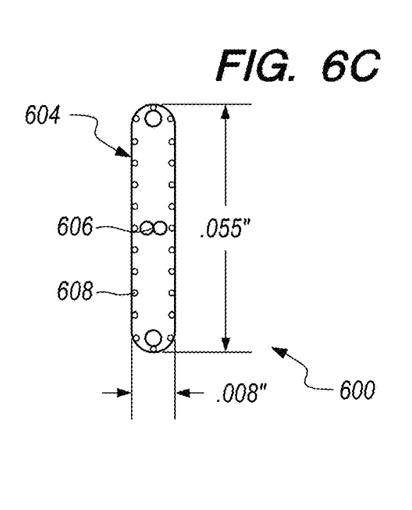
Figure 6D:
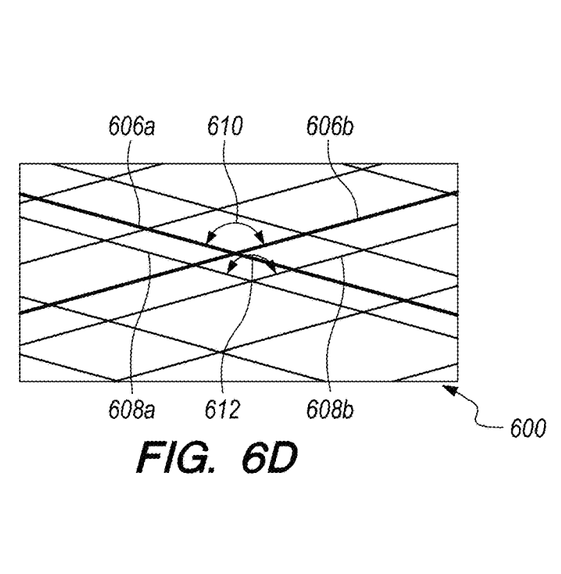
FIG. 6D is a detailed longitudinal schematic view.

The inner braided member 602 and the outer braided member 604 are configured such that a first angle 610 formed where the sections/filaments 606a, 606b, 606c, 606d of the RO wire 606 intersect is substantially equal to a second angle 612 formed where the sections/filaments 608a, 608b of the braid wire 608 intersect. As shown in FIG. 6D, the inner bent member 602 and the outer braided member 604 are also configured such that sections/filaments 606a, 606b, 606c, 606d of the RO wire 606 are substantially parallel to respective sections/filaments 608a, 608b of the braid wire 608. When the vaso-occlusive device 600 is in the constrained delivery configuration, sections/filaments 606a, 606b, 606c, 606d of the RO wire 606 form a third angle (not shown) and the sections/filaments 608a, 608b of the braid wire 608 form a fourth angle (not shown), that is substantially equal to the third angle.

As with the vaso-occlusive device 100 depicted in FIGS. 1A-1D, the substantial equivalence between the first and second angles 610, 612 in vaso-occlusive device 600 minimizes relative foreshortening of the inner braided member 602 compared to the outer braided member 604 when the vaso-occlusive device 600 transitions from the constrained delivery configuration to an unconstrained deployed configuration. Minimizing relative foreshortening during the transition between the delivery and deployed configurations minimizes changes in characteristics along the length of the vaso-occlusive device 600 and structural strain during the transition.

Figure 7:
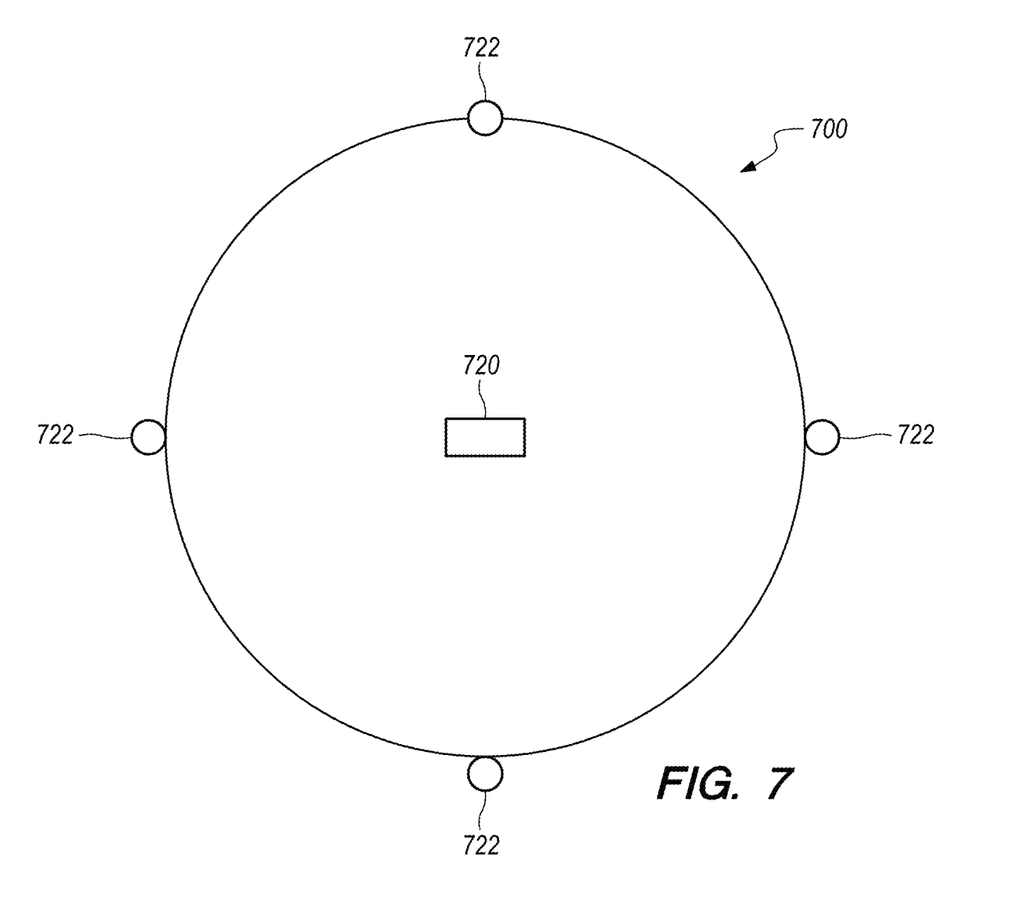
FIG. 7 is a schematic view of a braiding system configured to form the vaso-occlusive device depicted in FIG. 6A according to one embodiment.

FIG. 7 schematically depicts a braiding system 700 configured to form the vaso-occlusive device 600 depicted in FIGS. 6A-6D according to one embodiment. The braiding system 700 includes a mandrel 720 having a flat cross section and three bobbins 722.

In a first step of a method of forming the vaso-occlusive device 600 depicted in FIGS. 6A-6D according to one embodiment, the bobbins 722 are used to braid the one or more RO wires 606 to form the inner braided member 602 on top of the flat mandrel 720. In a second step, the one or more RO wires 606 are heat treated to set the shape of the inner braided member 602. In a third step, the bobbins 722 are used to braid the one or more braid wires 608 to form the outer braided member 604 on top of the inner braided member 602 and the flat mandrel 720. In a fourth step, the one or more braid wires 608 are heat treated to set the shape of the outer braided member 604. In a fifth step, the flat mandrel 720 is removed from the formed vaso-occlusive device 600.

While the vaso-occlusive devices 100, 200, 400, 600 depicted above have one, two, three, and four sections/filaments forming the respective inner bent member 102 and inner braided members 202, 402, 602, vaso-occlusive devices according to other embodiments may have up to about 12 sections/filaments forming an inner braided member. As described above, the inner and outer braided members can be modified to maintain a desired amount of flexibility with increasing numbers of sections/filaments in the inner braided members. Modifications to the inner and outer braided members include, but are not limited to, diameters or other indicators of cross-sectional area of sections/filaments and materials from which the sections/filaments are made.

Figure 8A:
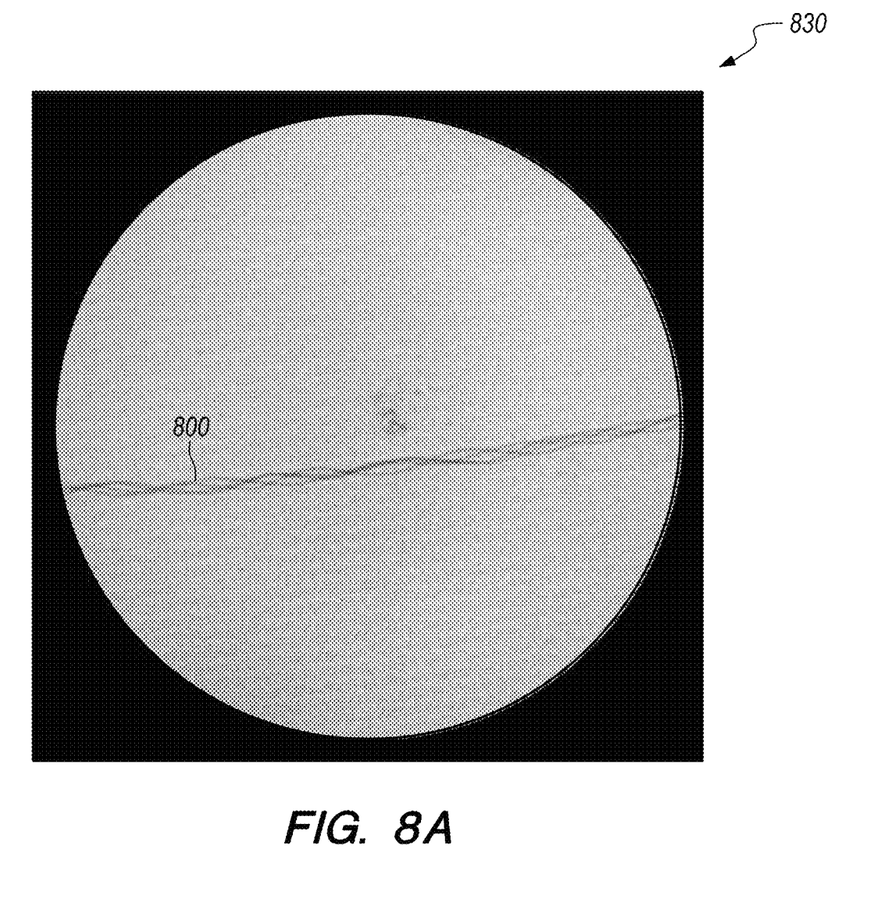
FIGS. 8A and 8B are images of vaso-occlusive devices in unconstrained, deployed configurations according to two embodiments.
Figure 8B:
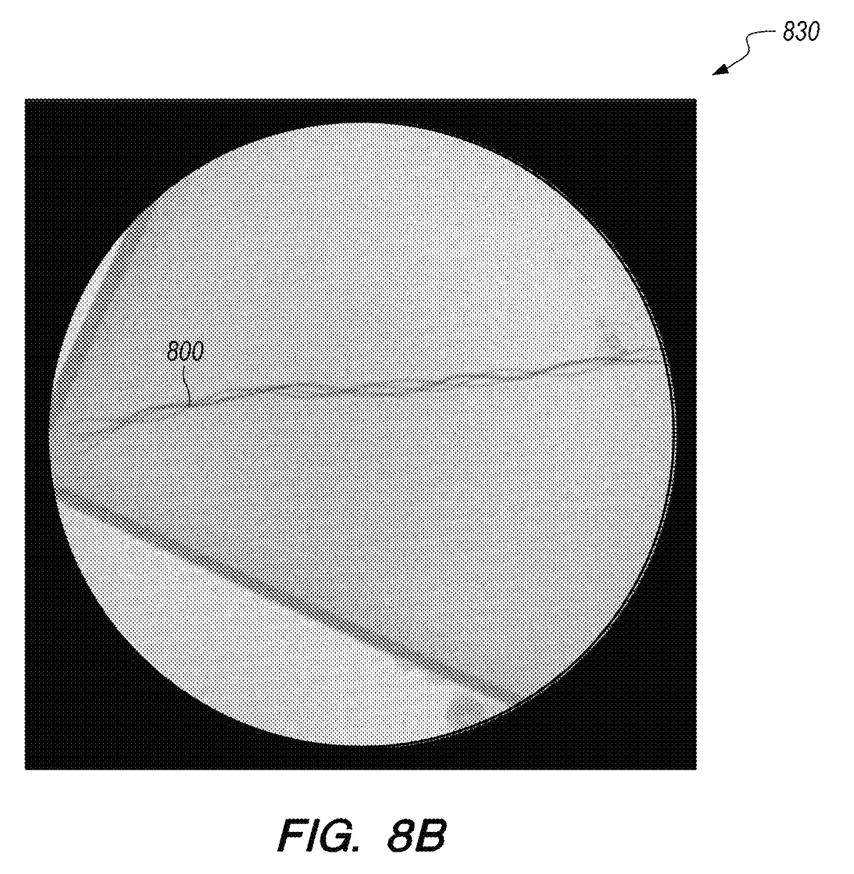

FIGS. 8A and 8B are fluoroscopic images 830 of a vaso-occlusive device 800 in an unconstrained deployed configuration constructed in accordance with one embodiment. As shown in FIG. 8A, the sections/filaments of the RO wire forming the inner braided member are visible using fluoroscopy. As shown in FIG. 8B, the vaso-occlusive device 800 has four sections/filaments of RO wire forming the inner braided member. While the vaso-occlusive device 800 shown in FIGS. 8A and 8B is generally linear in the unconstrained deployed configuration, vaso-occlusive devices according to other embodiments have non-linear secondary structures (e.g., spherical or cuboid) in the deployed configuration.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments, and are not intended as an exhaustive description of the disclosure or as a limitation on the scope of the disclosed subject embodiments, which is defined only by the appended claims and their equivalents. In addition, the respective illustrated embodiments need not each have all the aspects or advantages of features described herein. An aspect or an advantage described in conjunction with a particular embodiment of the disclosure is not necessarily limited to that embodiment and can be practiced in any other embodiments even if not so illustrated.

What is claimed is:

1. A vaso-occlusive device, comprising:
an inner braided member having an unconstrained deployed configuration and a constrained delivery configuration, the inner braided member comprising a first plurality of filaments made of a first material composition, wherein the first plurality of filaments extend longitudinally along the vaso-occlusive device in a zig-zag pattern defining a plurality of bends, each bend consisting of a single respective filament, and wherein at least one bend defines a first braid angle when the inner braided member is in the deployed configuration; and
an outer braided member disposed at least partially around the inner braided member, the outer braided member having an unconstrained deployed configuration and a constrained delivery configuration, wherein the outer braided member comprises a second plurality of filaments made of a second material composition different from the first material composition, wherein the first material composition has a greater radiopacity than the second material composition, wherein a pair of filaments of the second plurality define a second braid angle that is substantially equal to the first braid angle, when the outer braided member is in the deployed configuration.

2. The device of claim 1, wherein the filaments of one or both of the first plurality and second plurality have circular cross-sections with diameters ranging from about 0.0005" to about 0.003".

3. The device of claim 1, wherein the filaments of one or both of the first plurality and second plurality have non-circular cross-sections.

4. The device of claim 3, wherein the filaments of the first plurality have rectangular cross-sections.

5. The device of claim 1, wherein the first plurality of filaments consists of 2 to 12 filaments, and wherein the second plurality of filaments consists of 16-96 filaments.

6. The device of claim 5, wherein the second plurality of filaments consists of 24 filaments.

7. The device of claim 1, wherein the first material composition comprises one or more materials selected from the group consisting of a Pt group metal, Ta, Au, and alloys thereof, and wherein the second material composition comprises a superelastic alloy.

8. The device of claim 1, wherein the inner braided member and the outer braided member are attached to each other at respective first ends thereof.

9. The device of claim 1, wherein the braided occlusive device has a cross-section in the shape of a rectangle having semicircular opposing ends.

10. The device of claim 1, wherein the pair of filaments of the first plurality define a third braid angle when the inner braided member is in the delivery configuration, and wherein the pair of filaments of the second plurality define a fourth braid angle, substantially equal to the third braid angle, when the outer braided member is in the delivery configuration.

11. The device of claim 1, wherein the second material has a greater superelasticity than the first material.

12. A vaso-occlusive device, comprising:
an inner braided member having an unconstrained deployed configuration and a constrained delivery configuration, the inner braided member comprising a single braid wire having a plurality of segments made of a first material composition, wherein the single braid wire is bent at junctions between adjacent segments such that it forms a zig-zag pattern defining a plurality of bends, wherein each junction consists of only two respective segment of the single braid wire, and wherein at least one bend of the single braid wire between adjacent segments defines a first braid angle when the inner braided member is in the deployed configuration; and
an outer braided member disposed at least partially around the inner braided member, the outer braided member having an unconstrained deployed configuration and a constrained delivery configuration, wherein the outer braided member comprises a plurality of filaments made of a second material composition different from the first material composition, wherein the first material composition has a greater radiopacity than the second material composition, wherein a pair of filaments of the plurality of filaments define a second braid angle that is substantially equal to the first braid angle, when the outer braided member is in the deployed configuration.

13. The device of claim 12, wherein respective filaments of the plurality of filaments have circular cross-sections with diameters ranging from about 0.0005" to about 0.003".

14. The device of claim 12, wherein respective filaments of the plurality of filaments have non-circular cross-sections.

15. The device of claim 14, wherein the respective filaments have rectangular cross-sections.

16. The device of claim 12, wherein the plurality of segments consists of 2 to 12 segments, and wherein the plurality of filaments consists of 16-96 filaments.

17. The device of claim 12, wherein the first material composition comprises one or more materials selected from the group consisting of a Pt group metal, Ta, Au, and alloys thereof, and wherein the second material composition comprises a superelastic alloy.

18. The device of claim 12, wherein the inner braided member and the outer braided member are attached to each other at respective first and second ends thereof.

19. The device of claim 12, wherein the braided occlusive device has a cross-section in the shape of a rectangle having a semicircular opposing ends.

20. The device of claim 12, wherein the at least one bend of the single braid wire defines a third braid angle when the inner braided member is in the delivery configuration, and
wherein the pair of filaments of the plurality of filaments defines a fourth braid angle, substantially equal to the third braid angle, when the outer braided member is in the delivery configuration.

* * * * *